(12) United States Patent
Kobayashi et al.

(10) Patent No.: US 11,723,629 B2
(45) Date of Patent: Aug. 15, 2023

(54) ULTRASOUND DIAGNOSIS APPARATUS AND MEDICAL IMAGE PROCESSING METHOD

(71) Applicant: Canon Medical Systems Corporation, Otawara (JP)

(72) Inventors: Yukifumi Kobayashi, Yokohama (JP); Go Tanaka, Utsunomiya (JP); Satoshi Matsunaga, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 980 days.

(21) Appl. No.: 15/713,864

(22) Filed: Sep. 25, 2017

(65) Prior Publication Data

US 2018/0085094 A1    Mar. 29, 2018

(30) Foreign Application Priority Data

Sep. 26, 2016  (JP) .................................. 2016-186624

(51) Int. Cl.
*A61B 8/08*    (2006.01)
*A61B 8/14*    (2006.01)

(52) U.S. Cl.
CPC .......... *A61B 8/5223* (2013.01); *A61B 8/0833* (2013.01); *A61B 8/145* (2013.01); *A61B 8/483* (2013.01); *G06T 2207/30004* (2013.01)

(58) Field of Classification Search
CPC ..... A61B 8/5223; A61B 8/0833; A61B 8/145; A61B 8/483; G06T 2207/30004
See application file for complete search history.

(56) References Cited

U.S. PATENT DOCUMENTS

| | | | |
|---|---|---|---|
| 8,090,168 B2 | 1/2012 | Washburn et al. | |
| 2006/0195033 A1* | 8/2006 | Akimoto | A61B 6/00 600/429 |

(Continued)

FOREIGN PATENT DOCUMENTS

| | | |
|---|---|---|
| JP | 2008-100094 A | 5/2008 |
| JP | 2010-094224 | 4/2010 |

(Continued)

OTHER PUBLICATIONS

Office Action dated Aug. 11, 2020 in corresponding Japanese Patent Application No. 2016-186624, 5 pages.

*Primary Examiner* — Patricia J Park
(74) *Attorney, Agent, or Firm* — Oblon, McClelland, Maier & Neustadt, L.L.P.

(57) ABSTRACT

Accordion to one embodiment, an ultrasound diagnosis apparatus includes a volume data generating unit, an image generating unit, an MPR image generating unit, and a display controller. The volume data generating unit generates, based on position angle information of an ultrasound probe and echo data from the ultrasound probe, functional volume data of a subject accompanied with the position angle information. The image generating unit sequentially generates a sectional image of the subject based on the position angle information and the echo data. The MPR image generating unit generates an MPR image corresponding to the cross-section of the sectional image from the functional volume data based on the position angle information corresponding to the sectional image and the position angle information attached to the functional volume data. The display controller displays the sectional image and the MPR image in parallel or in a superimposed manner on a display.

14 Claims, 5 Drawing Sheets

(56) References Cited

U.S. PATENT DOCUMENTS

| | | | |
|---|---|---|---|
| 2009/0149759 A1* | 6/2009 | Baba | A61B 8/483 |
| | | | 600/454 |
| 2009/0187104 A1* | 7/2009 | Yamagata | G01S 7/52085 |
| | | | 600/443 |
| 2010/0286526 A1* | 11/2010 | Okamura | A61B 8/466 |
| | | | 600/443 |
| 2011/0077516 A1* | 3/2011 | Abe | A61B 8/463 |
| | | | 600/443 |
| 2013/0102903 A1* | 4/2013 | Tanaka | A61B 8/4444 |
| | | | 600/447 |
| 2013/0169632 A1* | 7/2013 | Sawayama | A61B 8/085 |
| | | | 345/419 |
| 2014/0236001 A1* | 8/2014 | Kondou | A61B 8/4254 |
| | | | 600/424 |
| 2015/0223782 A1* | 8/2015 | Yamagata | A61B 8/5292 |
| | | | 600/462 |
| 2015/0245819 A1* | 9/2015 | Yoshiara | A61B 8/0883 |
| | | | 600/424 |

FOREIGN PATENT DOCUMENTS

| | | |
|---|---|---|
| JP | 2011-24733 A | 2/2011 |
| JP | 2013-146376 A | 8/2013 |
| JP | 2013-240369 A | 12/2013 |
| JP | 2014-221161 A | 11/2014 |

* cited by examiner

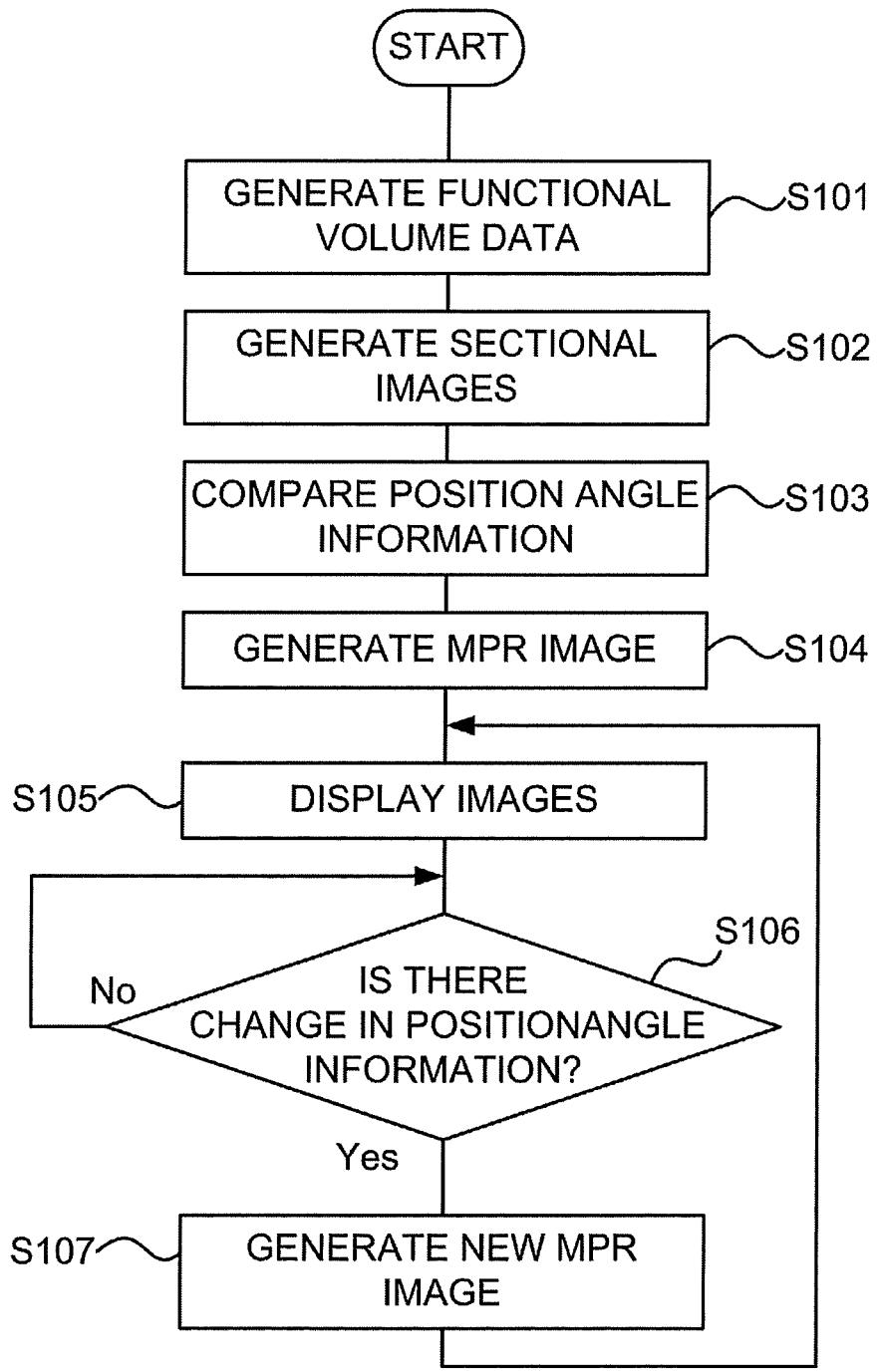

ULTRASOUND DIAGNOSIS APPARATUS AND MEDICAL IMAGE PROCESSING METHOD

CROSS-REFERENCE TO RELATED APPLICATION(S)

This application is based upon and claims the benefit of priority from Japanese Patent Application No. 2016-186624, filed Sep. 26, 2016; the entire contents of (all of) which are incorporated herein by reference.

FIELD

Embodiments described herein relate generally to an ultrasound diagnosis apparatus and a medical image processing method.

BACKGROUND

The ultrasound diagnosis apparatus transmits ultrasound waves to the inside of a subject's body through an ultrasound probe and receives reflected waves therefrom to acquire and visualize the biological information of the subject. Examples of images generated by the ultrasound diagnosis apparatus include a B mode image (morphological image) illustrating the morphology of the subject, a blood flow image (an example of a functional image) illustrating blood flow information of the subject, and a tissue property image (an example of a functional image) illustrating tissue properties such as the hardness of the tissue of the subject. These images are each generated as a two-dimensional image or a three-dimensional image according to the situation at the time of generating the image.

For example, during biopsy using a puncture needle or procedure of radiofrequency ablation (RFA), the ultrasound diagnosis apparatus successively generates morphological images and functional images simultaneously in parallel. Then, the ultrasound diagnosis apparatus sequentially aligns the morphological images and the functional images to display them. An operator such as a doctor or a technician performs the procedure while viewing the morphology of the subject represented by the morphological images as well as blood flow information and tissue properties represented by the functional images. For example, the operator views a blood flow image and figures out the position of the blood vessel. Besides, the operator views a tissue property image and figured out the position of the tissue the hardness of which is different from that of the surrounding tissue (e.g., the position of a tumor).

However, in order to sequentially generate, align, and display a plurality of types of images simultaneously in parallel, the ultrasound diagnosis apparatus has to perform a large number of processing steps, and the frame rate sometimes decreases. For example, in the procedure as described above, the insertion of a puncture needle may be a burden for a subject. Thus, there is a demand for a technology that enables the operator to perform the procedure while viewing images at a good frame rate.

BRIEF DESCRIPTION OF THE DRAWINGS

FIG. 5 is a flowchart illustrating the operation of the ultrasound diagnosis apparatus of the embodiment.

DETAILED DESCRIPTION

Figure 1:
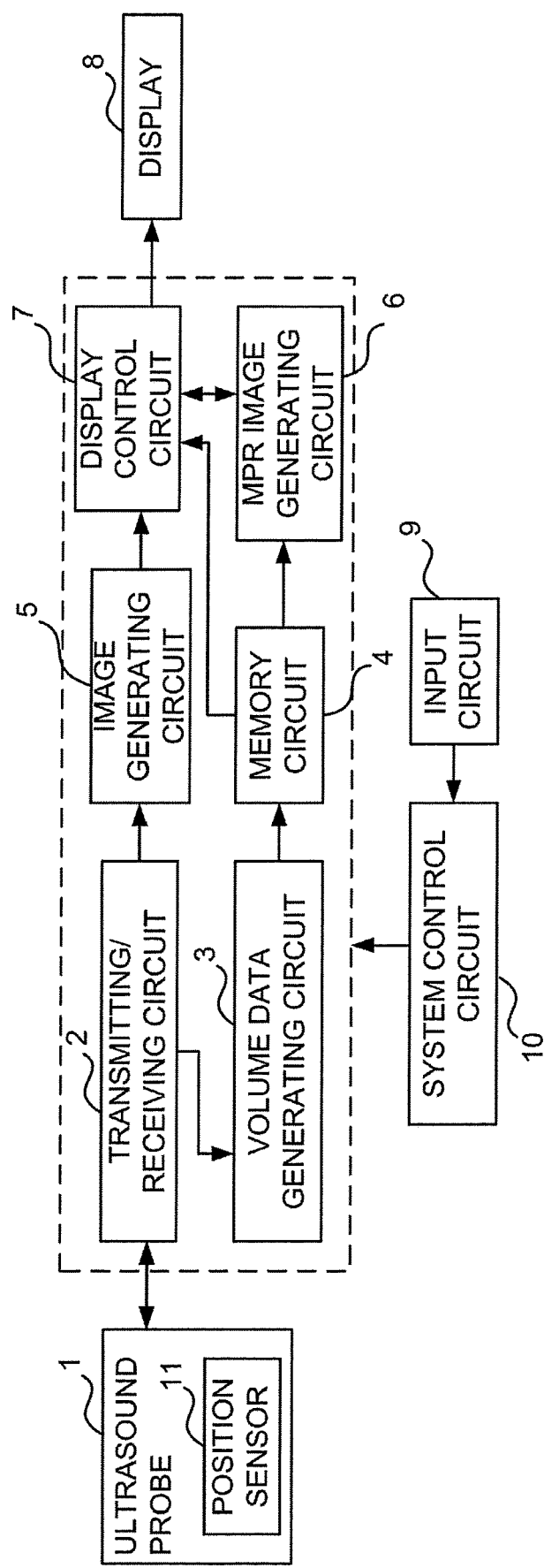
FIG. 1 is a block diagram illustrating a configuration of an ultrasound diagnosis apparatus according to an embodiment.

In general, according to one embodiment, an ultrasound diagnosis apparatus includes a volume data generating unit, an image generating unit, an MPR image generating unit, and a display controller. The volume data generating unit generates, based on position angle information of an ultrasound probe and echo data from the ultrasound probe, functional volume data of a subject accompanied with the position angle information. The image generating unit sequentially generates a sectional image of the subject based on the position angle information and the echo data. The MPR image generating unit generates an MPR image corresponding to the cross-section of the sectional image from the functional volume data based on the position angle information corresponding to the sectional image and the position angle information attached to the functional volume data. The display controller displays the sectional image and the MPR image in parallel or in a superimposed manner on a display.

Referring now to the drawings, a description is given of an ultrasound diagnosis apparatus and a medical image processing program according to embodiments.

FIG. 1 is a block diagram illustrating a configuration of an ultrasound diagnosis apparatus according to an embodiment. The ultrasound diagnosis apparatus of the embodiment includes an ultrasound probe 1, a transmitting/receiving circuit 2, a volume data generating circuit 3, a memory circuit 4, an image generating circuit 5, a multi planar reconstruction (MPR) image generating circuit 6, a display control circuit 7, a display 8, an input circuit 9, and a system control circuit 10.

The ultrasound probe 1 may be a one-dimensional array probe having an array of a plurality of ultrasound transducers arranged in the scanning direction, or a two-dimensional array probe having a plurality of ultrasound transducers two-dimensionally arranged. Incidentally, in the case of generating a three-dimensional image (sometimes referred to as volume data) indicating the three-dimensional area of a subject, a two-dimensional array probe is used. The ultrasound probe 1 transmits ultrasound waves to a subject and receives reflected waves from the subject as echo data. The ultrasound probe 1 includes a position sensor 11. The position sensor 11 sequentially detects the position and angle of the ultrasound probe 1 that is transmitting/receiving ultrasound waves and obtains position angle information indicating the position and angle detected. The ultrasound probe 1 attaches the position angle information to the echo data and outputs the echo data to the transmitting/receiving circuit 2.

Figure 2:
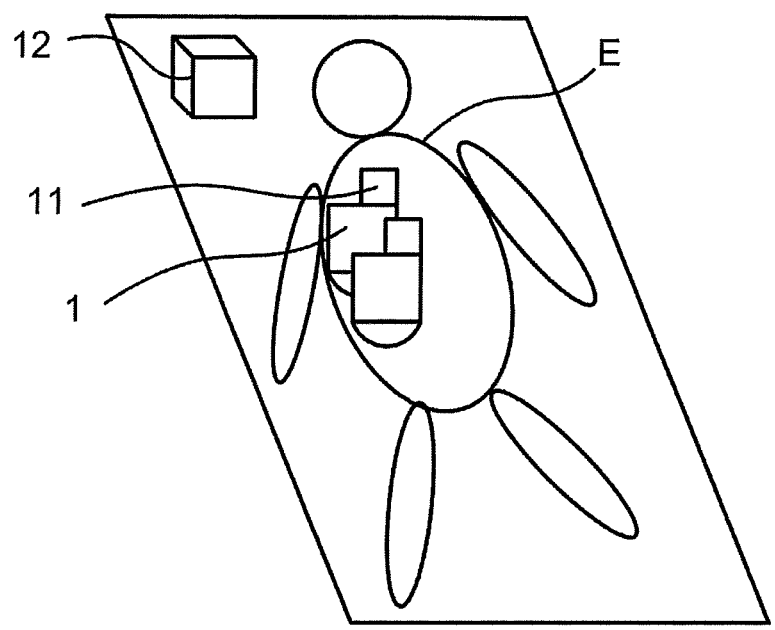
FIG. 2 is a schematic diagram illustrating a position sensor of the embodiment.

FIG. 2 is a schematic diagram schematically illustrating the position sensor 11. For example, when the ultrasound probe 1 transmit/receives ultrasound waves to/from a subject E, the position sensor 11 sequentially detects the position and angle of the ultrasound probe 1 concurrently with the transmission/reception. A transmitter 12 is arranged near the subject E. The position sensor 11 detects the position and angle with respect to the transmitter 12 as a reference to acquire position angle information indicating the position and angle of the ultrasound probe 1. As a concrete example of the hardware configuration of the position sensor 11 and the transmitter 12 may be cited an ordinary magnetic sensor system or an optical sensor system, and the installation location may be designed appropriately.

The transmitting/receiving circuit 2 supplies an electric signal to the ultrasound probe 1 to cause it to transmit ultrasound waves that have been beamformed to a predetermined focal point (i.e., subjected to transmission beamforming). In addition, the transmitting/receiving circuit 2 applies reception beamforming to the echo data from the ultrasound probe 1, and outputs it to the volume data generating circuit 3 as a received signal accompanied with the position angle information.

The volume data generating circuit 3 is a processor configured to generate functional volume data of the subject accompanied with position angle information based on the position angle information and the echo data from the ultrasound probe 1. For example, the volume data generating circuit 3 receives a received signal accompanied with the position angle information from the transmitting/receiving circuit 2, and generates the functional volume data. Examples of the functional volume data include blood flow volume data indicating blood flow information of the subject E and tissue property volume data indicating tissue properties of the subject E.

The volume data generating circuit 3 performs a Doppler process on the received signal and thereby generates blood flow volume data indicating the blood flow information of the subject. The accuracy and the like of the Doppler process are set in advance. Since the blood flow volume data is a three-dimensional image illustrating the blood flow, the operator can figure out the position of the blood vessel by visually checking the position where the blood flow occurs. In addition, the volume data generating circuit 3 applies tissue elasticity imaging (elastography) to the received signal and thereby generates tissue property volume data indicating the tissue properties of the subject. Examples of the tissue properties include the hardness of tissue. Since the tissue property volume data is a three-dimensional image that three-dimensionally illustrates the distribution of the tissue properties (e.g., the hardness of tissue) of the subject, the operator can figure out the position of the tissue the hardness of which is different from that of the surrounding tissue (e.g., the position of a tumor). The volume data generating circuit 3 outputs the blood flow volume data and the tissue property volume data accompanied with the position angle information to the memory circuit 4. The memory circuit 4 is formed of a memory or a storage device, and stores the blood flow volume data and the tissue property volume data from the volume data generating circuit 3.

In this way, after the functional volume data accompanied with the position angle information is generated and stored, ultrasound waves are transmitted/received (sometimes referred to as scan) in a biopsy or RFA procedure. In the following, an example is described in which two-dimensional morphological images are sequentially generated in a procedure. The ultrasound probe 1 transmits and receives ultrasound waves concurrently with the procedure, and the position sensor 11 acquires position angle information concurrently with the procedure. The ultrasound probe 1 outputs echo data accompanied with the position angle information to the transmitting/receiving circuit 2. The transmitting/receiving circuit 2 applies reception beamforming to the echo data, and outputs it to the image generating circuit 5 as a received signal accompanied with the position angle information.

The image generating circuit 5 is a processor that sequentially generates sectional images of the subject based on the position angle information and the echo data at the time of scanning after the generation of the functional volume data. The frame rate at which the sectional images are sequentially generated is set in advance. For example, the image generating circuit 5 performs band-pass filtering on the received signal from the transmitting/receiving circuit 2. Thereafter, the image generating circuit 5 detects the envelope of the output signal, and performs a compression process on the detected data by logarithmic conversion. The image generating circuit 5 performs a scan conversion process on the received signal (ultrasound raster data) that has been subjected to these processes to generate a B mode image (an example of a sectional image) indicating the morphology of the cross-section of the tissue of the subject. Further, the image generating circuit 5 attaches the position angle information, which is attached to the received signal from the transmitting/receiving circuit 2, to the B mode image. Normally, the position and angle of the ultrasound probe correspond to the position and angle of the cross-section of the B-mode image. Therefore, the position and angle indicated by the position angle information attached to the B mode image correspond to the position and angle of the cross-section at the time of scanning. Each time generating a B-mode image accompanied with position angle information, the image generating circuit 5 outputs it to the MPR image generating circuit 6 and the display control circuit 7.

The MPR image generating circuit 6 is a processor that generates an MPR image corresponding to the cross-section of the sectional image from functional volume data based on the position angle information corresponding to the sectional image and the position angle information attached to the functional volume data. For example, the MPR image generating circuit 6 reads the functional volume data generated in advance from the memory circuit 4. The MPR image generating circuit 6 compares the position angle information attached to the functional volume data with the position angle information attached to the B mode image generated by the image generating circuit 5. The MPR image generating circuit 6 applies an MPR process corresponding to the cross-section of the B mode image to the functional volume data, and thereby specifies a cross-section corresponding to the cross-section of the B mode image in the functional volume data. Then, the MPR image generating circuit 6 generates an MPR image indicating the cross-section specified. The MPR image generating circuit 6 outputs the MPR image to the display control circuit 7. The MPR image generating circuit 6 may generate an MPR image from blood flow volume data or tissue property volume data as an example of the functional volume data, or from both of them.

The B mode image is generated with respect to each frame rate and output to the MPR image generating circuit 6. The MPR image generating circuit 6 generates a new MPR image when there is a change in position angle information attached to the B mode image received after generating the first MPR image. After generating the first MPR image, the MPR image generating circuit 6 compares position angle information attached to a B mode image newly received from the image generating circuit 5 and position angle information attached to an MPR image generated most recently. When there is a change in these pieces of position angle information, the MPR image generating circuit 6 generates, from the functional volume data, an MPR image corresponding to the cross-section of the position angle information attached to a B mode image newly received, and outputs it to the display control circuit 7. When there is no change in the pieces of position angle information, the MPR image generating circuit 6 does not generate a new MPR image. In this manner, the MPR image generating circuit 6 generates an MPR image depending on whether there is a change in the position angle information. Thereby, an MPR cross-section corresponding to the cross-section being scanned is generated following the movement of the ultrasound probe 1 that is performing scanning. As a change amount that serves as a threshold value for determining whether there is a change in the position angle information, a threshold value relating to the change amount of the position and a threshold value relating to the change amount of the angle are determined in advance. When there is a change equal to or larger than the threshold value, the MPR image generating circuit 6 determines that a change occurs in the position angle information.

Besides, there is a case that a period between a scan in which the functional volume image is generated and the subsequent scan is long. As an example of this case may be cited a case where some days are left due to the follow-up of a procedure or the like. In this case, even if the subject is placed on the bed at the same position and in the same posture as in the procedure, the positional relationship (relative position) between the transmitter 12 and the subject E differs between scans of both, and the orientation and the reference position of the position angle information of both may be shifted (i.e., the coordinate system is shifted). In this case, the MPR image generating circuit 6 extracts characteristic sites (e.g., xiphoid process, etc.) depicted in the B mode image and the functional volume data and aligns the sites to thereby match the coordinate systems of both of them. General processing techniques may be applied to the extraction process of characteristic sites and the alignment process.

The display control circuit 7 is a processor that displays the sectional image and the MPR image in parallel or in a superimposed manner on the display 8. For example, the display control circuit 7 displays the B mode image from the image generating circuit 5 and the MPR image from the MPR image generating circuit 6 in parallel or in a superimposed manner on the display 8. The setting of the parallel display and the superimposed display may be determined in advance or the display modes may be switched by an operation of the operator.

The display 8 is an example of the display in the claims. The display 8 is formed of a display device such as a liquid crystal display (LCD) or an organic electro-luminescence (EL) display.

Figure 3:
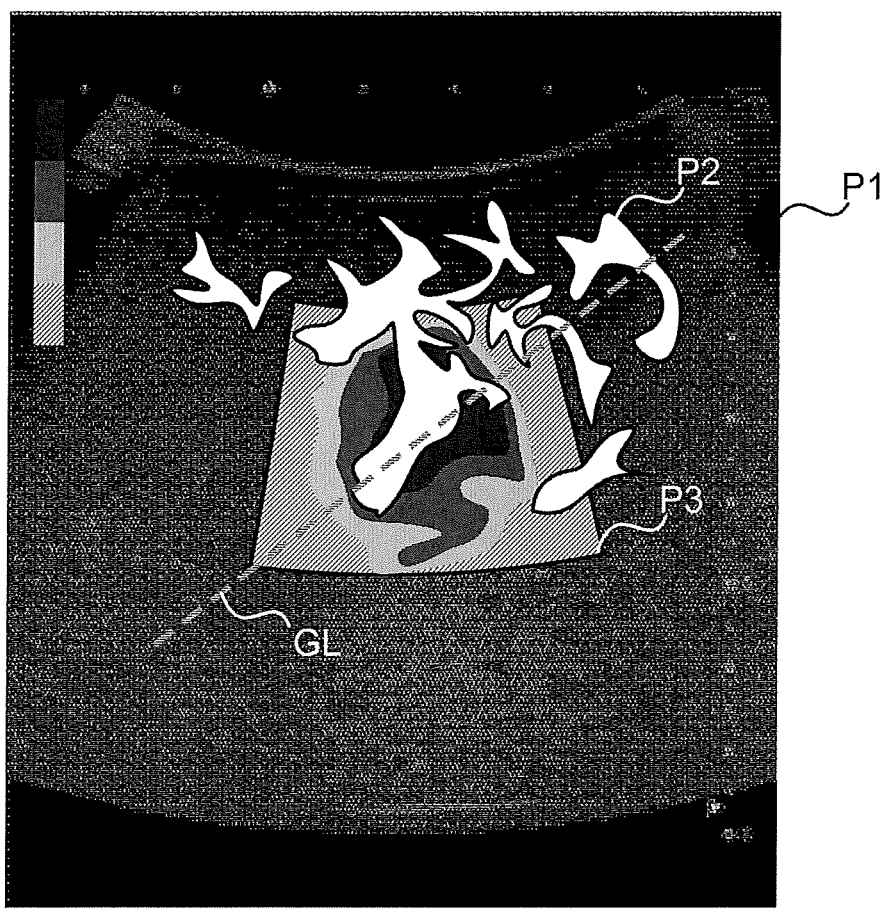
FIG. 3 is a schematic diagram illustrating images displayed as being superimposed in the embodiment.

FIG. 3 is a schematic diagram schematically illustrating images displayed as being superimposed. In the following, an example is described in which a B mode image P1 as the sectional image of the subject E, an MPR image P2 generated from blood flow volume data, and an MPR image P3 generated from tissue property volume data are displayed as being superimposed. The display control circuit 7 checks position angle information attached to the B mode image P1, position angle information attached to the MPR image P2, and position angle information attached to the MPR image P3 to thereby align the images and display them in a superimposed manner. The layer order of the superimposed display, the type of images to be displayed, and the transparency of each image may be set in advance, or may be switchable by an operation of the operator.

As the images are aligned and displayed as being superimposed in this manner, the operator can perform a procedure while checking the morphology of tissue with the B mode image, the position of the blood vessel with the MPR image from the blood flow volume data, and the position of the tissue the hardness or the like of which is characteristic and different from that of the surrounding tissue with the MPR image from tissue property volume data. In the example of the embodiment, the scan during a procedure is a scan for generating the B mode image, and the MPR image is an image based on the volume data generated in advance. Thereby, the ultrasound diagnosis apparatus of the embodiment can sequentially display a plurality of types of images while preventing a decrease in the frame rate. Therefore, the operator can perform a procedure while visually checking images at a good frame rate.

The display control circuit 7 may generate a guideline index GL indicating the insertion path of the puncture needle, and display the guideline index as being further superimposed. For example, upon receipt of an operation signal provided by the operator through the input circuit 9, the display control circuit 7 aligns the insertion start position of the puncture needle and a target position indicating the position of a lesion or the like with the image being displayed. At this time, the display control circuit 7 compares position information attached to each image being displayed with the insertion start position and the target position indicated by the operation signal, thereby performing the alignment. The display control circuit 7 generates a linear marker that connects the insertion start position and the target position as the guideline index GL and displays it as being superimposed on each image. With this, the operator can perform a procedure while visually checking the insertion path. Note that the guideline index GL is not limited to a linear index, and, for example, may be an index indicating the insertion start position and the target position in another shape.

Figure 4:
FIG. 4 is a schematic diagram illustrating images displayed in parallel in the embodiment.

Incidentally, the display control circuit 7 may appropriately display the images in parallel. FIG. 4 is a schematic diagram schematically illustrating images displayed in parallel. FIG. 4 illustrates an example in which, together with the superimposed image illustrated in FIG. 3, the superimposed image of the B mode image P1 and the guideline index GL, the MPR image P2 generated from the blood flow volume data, and the MPR image P3 generated from the tissue property volume data are displayed in parallel in a 2.times.2 display layout. The types of images displayed in display frames of the display layout and the types of images superimposed in each of the display frames may be selected appropriately by operation input by the operator. Examples of the types of images displayed include volume rendering images of blood flow volume data and volume rendering images of tissue property volume data. If multi-plane scanning is performed during the procedure, a B mode image illustrating a cross-section different from the cross-section of the B mode image P1 may be displayed in any one of the display frames. Thereby, the operator can perform the procedure while appropriately selecting desirable images.

The input circuit 9 is an example of the operation unit in the claims. The input circuit 9 receives operation by an operator such as a doctor, a technician, or the like, and outputs a signal corresponding to the content of the operation to the system control circuit 10. The input circuit 9 includes, for example, a trackball, a switch button, a mouse, a keyboard, a touch command screen, a sensitivity time control (STC) slide volume, and the like.

The system control circuit 10 controls each part of the ultrasound diagnosis apparatus based on an operation signal received through the input circuit 9 and a medical image processing program stored in advance. For example, the system control circuit 10 stores in advance a program that implements a medical image processing method corresponding to the operation illustrated in the flowchart of FIG. 5 and executes it.

The term "processor" as used herein refers to a circuit such as, for example, a central processing unit (CPU), a graphics processing unit (GPU), an application specific integrated circuit (ASIC), a programmable logic device including a simple programmable logic device (SPLD) and a complex programmable logic device (CPLD), a field programmable gate array (FPGA), or the like. The processor reads programs out of a storage medium and executes them to thereby realize the functions. The programs need not necessarily be stored in a storage medium, but may be directly incorporated in the circuit of the processor. In this case, the processor realizes the functions by reading and executing the programs incorporated in the circuit. Each processor of the embodiment need not necessarily be configured as a single circuit. A plurality of independent circuits may be combined to form a single processor for implementing the functions. Besides, a plurality of constituent elements in FIG. 1 may be integrated into one processor to realize the functions.

FIG. 5 is a flowchart illustrating the operation of the ultrasound diagnosis apparatus according to the embodiment.

Step S101: The ultrasound probe 1 transmits ultrasound waves to the subject and receives reflected waves from the subject as echo data. The ultrasound probe 1 attaches position angle information to the echo data and outputs the echo data to the transmitting/receiving circuit 2. The transmitting/receiving circuit 2 applies reception beamforming to the echo data from the ultrasound probe 1 and outputs it to the volume data generating circuit 3 as a received signal accompanied with the position angle information. Based on the position angle information and the echo data from the ultrasound probe 1, the volume data generating circuit 3 generates blood flow volume data and tissue property volume data of the subject accompanied with the position angle information. The volume data generating circuit 3 outputs the blood flow volume data and the tissue property volume data accompanied with the position angle information to the memory circuit 4.

Step S102: At the time of scanning, the image generating circuit 5 sequentially generates sectional images of the subject based on the position angle information and the echo data. For example, the image generating circuit 5 generates a B mode image and attaches position angle information to the B mode image. Each time generating a B-mode image accompanied with position angle information, the image generating circuit 5 outputs it to the MPR image generating circuit 6 and the display control circuit 7.

Step S103: The MPR image generating circuit 6 reads functional volume data generated in advance from the memory circuit 4. The MPR image generating circuit 6 compares the position angle information attached to the functional volume data with the position angle information attached to the B mode image from the image generating circuit 5.

Step S104: The MPR image generating circuit 6 applies an MPR process corresponding to the cross-section of the B mode image to the functional volume data, and thereby generates an MPR image corresponding to the cross-section of the B mode image. The MPR image generating circuit 6 outputs the MPR image to the display control circuit 7.

Step S105: The display control circuit 7 displays the B mode image from the image generating circuit 5 and the MPR image from the MPR image generating circuit 6 in parallel or in a superimposed manner on the display 8.

Step S106: The MPR image generating circuit 6 compares position angle information attached to a B mode image newly received from the image generating circuit 5 and position angle information attached to an MPR image generated most recently to determine whether there is a change in the pieces of position angle information.

Step S107: When there is a change in the position angle information as a result of comparison (Yes in step S106), the MPR image generating circuit 6 generates an MPR image corresponding to the cross-section of the position angle information attached to the B mode image newly received based on the functional volume data, and outputs it to the display control circuit 7.

With the ultrasound diagnosis apparatus and the medical image processing program of at least one embodiment described above, a plurality of types of images can be sequentially displayed while the frame rate is prevented from falling.

Although the procedure is described above as being performed while the ultrasound diagnosis apparatus is performing scanning, the operator may perform the procedure while visually checking X-ray CT images or MR images by transferring functional volume data generated in advance to another medical image diagnosis apparatus (e.g., X-ray CT apparatus, MRI apparatus). At this time, in order to align the functional volume data with the X-ray CT images or the MR images, an uncharacteristic site is extracted from each image and the alignment is performed with reference to the position of the extracted site.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus, comprising:
 an ultrasound probe configured to output position angle information and echo data, the position angle information being acquired from a position sensor that detects a position and an angle of the ultrasound probe; and
 processing circuitry configured to:
 generate, based on first position angle information and first echo data output from the ultrasound probe by a first scan, functional volume data of a subject;
 store the functional volume data in a storage;
 sequentially generate a sectional image indicating morphology of the subject based on second echo data sequentially output from the ultrasound probe by a second scan that is performed after the first scan;
 generate a functional MPR image corresponding to the sectional image based on second position angle information corresponding to the second echo data and on the functional volume data stored in the storage;
 generate a new functional MPR image, after generating the functional MPR image, when there is a change in the second position angle information corresponding to the second echo data, the new functional MPR image corresponding to the changed second position angle information; and display the sectional image based on the second echo data corresponding to the changed second position angle information, and the new functional MPR image in parallel or in a superimposed manner on a display.

2. The ultrasound diagnosis apparatus of claim 1, wherein the processing circuitry is further configured to generate blood flow volume data indicating blood flow information of the subject or tissue property volume data indicating tissue properties of the subject as the functional volume data.

3. The ultrasound diagnosis apparatus of claim 2, wherein the processing circuitry is further configured to:
generate the blood flow volume data and the tissue property volume data; and
display the new functional MPR image generated from the blood flow volume data and indicating a position of a blood vessel of the subject, the new functional MPR image generated from the tissue property volume data and indicating hardness of tissue of the subject, and the sectional image in parallel or in the superimposed manner on the display.

4. The ultrasound diagnosis apparatus of claim 1, wherein the processing circuitry is further configured to change transparency of the new functional MPR image and display the new functional MPR image on the display.

5. The ultrasound diagnosis apparatus of claim 1, wherein the processing circuitry is further configured to:
generate a guideline index indicating an insertion path of a puncture needle on the sectional image being displayed based on an operation signal and the second position angle info ration of the sectional image being displayed, wherein the operation signal indicates an insertion start position and a target position; and
display the guideline index so as to be superimposed on the sectional image on the display.

6. The ultrasound diagnosis apparatus of claim 5, wherein the guideline index also indicates the insertion start position of the puncture needle.

7. The ultrasound diagnosis apparatus of claim 1, wherein the processing circuitry is configured to generate the functional volume data accompanied with the first position angle information.

8. The ultrasound diagnosis apparatus of claim 1, wherein the processing circuitry is configured to generate the new functional MPR image corresponding to the sectional image from the functional volume data stored in the storage by comparing the second position angle information corresponding to the second echo data to the first position angle information of the functional volume data stored in the storage.

9. The ultrasound diagnosis apparatus of claim 1, wherein the processing circuitry is configured to, when there is the change in the second position angle information corresponding to the second echo data, generate the new functional MPR image corresponding to the sectional image from the functional volume data stored in the storage by comparing the second position angle information corresponding to the second echo data to the first position angle information of the functional volume data stored in the storage.

10. The ultrasound diagnosis apparatus of claim 1, wherein the processing circuitry is further configured to generate the new functional MPR image when an amount of change in the second position angle information corresponding to the second echo data with respect to the second position angle information corresponding to the functional MPR image is equal to or larger than a threshold value.

11. The ultrasound diagnosis apparatus of claim 1, wherein the processing circuitry is further configured to:
store the functional volume data and the first position angle information in the storage;
sequentially generate the sectional image indicating morphology of the subject based on the second position angle information and the second echo data sequentially output from the ultrasound probe by the second scan;
generate the functional MPR image corresponding to the sectional image from the functional volume data stored in the storage based on the second position angle information corresponding to the second echo data and on the first position angle information of the functional volume data stored in the storage; and
when there is a change in the second position angle information corresponding to the second echo data with respect to the second position angle information corresponding to the functional MPR image after generating the functional MPR image, generate the new functional MPR image corresponding to the changed second position angle information.

12. A medical image processing method, comprising:
receiving, from an ultrasound probe, position angle information and echo data, the position angle information being acquired from a position sensor that detects a position and an angle of the ultrasound probe;
generating, based on first position angle information and first echo data received from the ultrasound probe by a first scan, functional volume data of a subject;
storing the functional volume data in a storage;
sequentially generating a sectional image indicating morphology of the subject based on second echo data sequentially received from the ultrasound probe by a second scan that is performed after the first scan;
generating a functional MPR image corresponding to the sectional image based on second position angle information corresponding to the second echo data and on the functional volume data stored in the storage;
generating a new functional MPR image after generating the functional MPR image change, when there is a change in the second position angle information corresponding to the second echo data, the new functional MPR image corresponding to the changed second position angle information; and
displaying the sectional image based on the second echo data corresponding to the changed second position angle information, and the new functional MPR image in parallel or in a superimposed manner on a display.

13. The medical image processing method of claim 12, further comprising generating blood flow volume data indicating blood flow information of the subject or tissue property volume data indicating tissue properties of the subject as the functional volume data.

14. The medical image processing method of claim 13, further comprising:
generating the blood flow volume data and the tissue property volume data; and
displaying the new functional MPR image generated from the blood flow volume data and indicating a position of a blood vessel of the subject, the new functional MPR image generated from the tissue property volume data and indicating hardness of tissue of the subject, and the sectional image in parallel or in the superimposed manner on the display.

\* \* \* \* \*